(12) United States Patent
Raoult et al.

(10) Patent No.: US 7,141,658 B1
(45) Date of Patent: Nov. 28, 2006

(54) SINGLE STRANDED OLIGONUCLEOTIDES, PROBES, PRIMERS AND METHOD FOR DETECTING SPIROCHETES

(75) Inventors: Didier Raoult, Marseille (FR); Michel Drancourt, Marseille (FR)

(73) Assignee: bioMerieux, Marcy l'Etoile (FR)

( * ) Notice: Subject to any disclaimer, the term of this patent is extended or adjusted under 35 U.S.C. 154(b) by 1012 days.

(21) Appl. No.: 10/070,134

(22) PCT Filed: Sep. 8, 2000

(86) PCT No.: PCT/FR00/02481

§ 371 (c)(1),
(2), (4) Date: Apr. 15, 2002

(87) PCT Pub. No.: WO01/20028

PCT Pub. Date: Mar. 22, 2001

(30) Foreign Application Priority Data

Sep. 10, 1999 (FR) .................................. 99 11493

(51) Int. Cl.
*C07H 21/02* (2006.01)
*C12Q 1/68* (2006.01)

(52) U.S. Cl. ......................................... 536/23.1; 435/6

(58) Field of Classification Search ............... 536/23.1; 435/6
See application file for complete search history.

(56) References Cited

U.S. PATENT DOCUMENTS 5,786,147 A 7/1998 Mabilat et al.
2006/0051426 A1* 3/2006 Golomb et al. ............. 424/491

FOREIGN PATENT DOCUMENTS

| WO | WO 96/23071 | 8/1996 |
| WO | WO 97/11162 | 3/1997 |
| WO | WO 98/44130 | 10/1998 |
| WO | WO 98/58943 | 12/1998 |
| WO | WO 98/59034 | 12/1998 |

OTHER PUBLICATIONS

Alaibac et al., "High incidence of a Tnucleotide at the second position of codon 97 in Vdelta2-Jdelta junctional sequences of human normal skin gamma-delta T-cells" Molecular Immunology, vol. 33, 1996, pp. 1035-1038.
Alekshun et al., "Molecular cloning and characterization of Borrelia burgdoferi rpoB", Gene: An International Journal on Genes and Genomes, GB, Elsevier Science Publishers, Barking, vol. 186, No. 2, Feb. 28, 1997, pp. 227-235, XP004093305.
Mollet et al., "ropB sequence analysis as a novel basis for bacterial identification", Molecular Microbiology, Dec. 1997, XP000920777.
Renesto et al., "ropB gene analysis as a novel strategy for identification of spirochetes from the genera Borrelia, Treponema, and Leptospira", Journal of Clinical Microbiology, vol. 38, No. 6, Jun. 2000, pp. 2200-2203, XP002155811.

* cited by examiner

*Primary Examiner*—Mark Navarro
(74) *Attorney, Agent, or Firm*—Oliff & Berridge, PLC (57) ABSTRACT

The invention concerns single stranded oligonucleotides comprising a sequence of at least 12 consecutive nucleotide motifs contained in one of the sequences SEQ ID NO: 1 to SEQ ID NO: 4 wherein "n" represents an identical or different nucleotide selected among inosine or an equimolar mixture of 4 different nucleotides selected among a, t, c or g, and among oligonucleotides complementary thereto. The invention also concerns using the oligonucleotides to detect bacteria of the Spirochaetales order. The invention is based on the use of specifically defined sequences in the rpoB gene of spirochetes coding for the beta subunit of the bacterial RNA polymerase.

11 Claims, 2 Drawing Sheets

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (6)..(6)
<223> OTHER INFORMATION: n = inosine or an equimolar  mixture of a, t, g
      and c
<220> FEATURE:
<221> NAME/KEY: misc_feature
<222> LOCATION: (9)..(9)
<223> OTHER INFORMATION: n = inosine or an equimolar  mixture of a, t, g
      and c
<220> FEATURE:
<221> NAME/KEY: misc_feature
<222> LOCATION: (12)..(12)
<223> OTHER INFORMATION: n = inosine or an equimolar  mixture of a, t, g
      and c

<400> SEQUENCE: 1
cttggnccng gnggactttc                                                20

<210> SEQ ID NO 2
<211> LENGTH: 21
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (7)..(7)
<223> OTHER INFORMATION: n = inosine or an equimolar  mixture of a, t, g
      and c
<220> FEATURE:
<221> NAME/KEY: misc_feature
<222> LOCATION: (10)..(10)
<223> OTHER INFORMATION: n = inosine or an equimolar  mixture of a, t, g
      and c
<220> FEATURE:
<221> NAME/KEY: misc_feature
<222> LOCATION: (13)..(13)
<223> OTHER INFORMATION: n = inosine or an equimolar  mixture of a, t, g
      and c

<400> SEQUENCE: 2
agaaatnaan atngcatcct c                                              21

<210> SEQ ID NO 3
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
```

```
<222> LOCATION: (6)..(6)
<223> OTHER INFORMATION: n = inosine or an equimolar  mixture of a, t, g
      and c
<220> FEATURE:
<221> NAME/KEY: misc_feature
<222> LOCATION: (12)..(12)
<223> OTHER INFORMATION: n = inosine or an equimolar  mixture of a, t, g
      and c
<220> FEATURE:
<221> NAME/KEY: misc_feature
<222> LOCATION: (18)..(18)
<223> OTHER INFORMATION: n = inosine or an equimolar  mixture of a, t, g
      and c

<400> SEQUENCE: 3
gggtgnattt tntcatcnac                                              20

<210> SEQ ID NO 4
<211> LENGTH: 17
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (6)..(6)
<223> OTHER INFORMATION: n = inosine or an equimolar  mixture of a, t, g
      and c
<220> FEATURE:
<221> NAME/KEY: misc_feature
<222> LOCATION: (9)..(9)
<223> OTHER INFORMATION: n = inosine or an equimolar  mixture of a, t, g
      and c
<220> FEATURE:
<221> NAME/KEY: misc_feature
<222> LOCATION: (15)..(15)
<223> OTHER INFORMATION: n = inosine or an equimolar  mixture of a, t, g
      and c

<400> SEQUENCE: 4
gcttcnagng cccanac                                                 17

<210> SEQ ID NO 5
<211> LENGTH: 3876
<212> TYPE: DNA
<213> ORGANISM: Leptospira biflexa
<220> FEATURE:
<221> NAME/KEY: misc_feature
<222> LOCATION: (21)..(21)
<223> OTHER INFORMATION: n = inosine or an equimolar  mixture of a, t, g
      and c
<220> FEATURE:
<221> NAME/KEY: misc_feature
<222> LOCATION: (29)..(29)
<223> OTHER INFORMATION: n = inosine or an equimolar  mixture of a, t, g
      and c
<220> FEATURE:
<221> NAME/KEY: misc_feature
<222> LOCATION: (35)..(35)
<223> OTHER INFORMATION: n = inosine or an equimolar  mixture of a, t, g
      and c

<400> SEQUENCE: 5
gctgatatta agaaaaaact ncgaaggtnt tgggnctcaa gtagaagttg ctggctgccc    60
ggttaatcgg ttgcccaatt tttaaaccca gtcttcaaaa acttagaggc agggaggccg   120
taggcgtccc cacctctatt ttttcgttta tcataccatc tattattttg acgtctctag   180
ggagagtatt ccatgcatac ccgaatgcaa attagaaacc gggtaaattt cggtaaaatt   240
accgacctca atttacttcc taatcttatc tacgtacaga aaaaatcctt tgattggttc   300
ctccagtcgg aagtgaaaga tccgacgaaa cgtttgaacc aagggttgga agcggtattc   360
```

-continued

```
cgcgaatcat tcccaatcga atcaccaaac aacgatatgg tcatggaata tggccattac    420
gttttgggag agccgaaacg cgatccccaa gagtgcaaag acactgattc ttcttttgct    480
gttccactga aagcagtcat ccgtctcatc atcaaagaca ccggtgaaat ccgcgaacaa    540
gtcgtctaca tgggtgacct tcctgtgatg acagaccacg gaactttcat catcaatggt    600
gccgaaaggg tagtggtaag ccagttacac cgatctcctg gtattttctt ttcgtatgac    660
caagtacgag atacattttc tgcccgagtg attccttatc gtggatcatg gttagaattc    720
gagatggaca acaagggaat cctcgttgcc aaaatcgacc gtaagaaaaa attcccagcg    780
actctccttg tgaaagccat gggtatggga acaaacgaag aagtacttcg cctttttctac    840
ggatctagca aaatgaaaat cgctggtgcc aatccaaaag acctcaaacg tctgattggc    900
cgccgaacca ttgcggatat tatcaatatg gaaaccggtg aggtaatgct cgatgctggt    960
tccaaaatta acgaagacaa tatctccatc cttcgtgaaa tgaaggtaaa agaagtggat   1020
gtcatcgaat ttccaaaagg aaaagacaat ccagttctca tcaattgcct agaaaaagac   1080
ggagtgaacg actacgagga tgcagtgaaa aaatttcaca cgatcatgcg tccaggggaa   1140
ccttctacga ttgaaaacgc ggaagctgag ttaaaacgcc tctttttctc tccaaaaacg   1200
tttgatttag gaattgttgg tcgttacaaa atcaatagca aattcgagtt caacaatcca   1260
aaagaattct caaaagcaga tgatcgggtt ctccgaaaac aagacatcat cgaaaccgtt   1320
cgttaccttg tgatgcttat gtcagaagcg gaaaattatt acccagatga cattgaccac   1380
ttaggaaaca gaaggatccg ttcggtgggg aactcatcg ctaaccaatt gaaacttggt   1440
ttttccagag tggaacgagt catcaaagaa aggatgacag tacaggagcc ggaacaacaa   1500
actcctcagc ttcttatctc catcaaacca atcacagcag tgatcaatga gttttttgga   1560
tcttcgcaac tctctcagtt tatggaccaa accaatccct tggcagaact acgcacaaaa   1620
cgtaggttaa acgctcttgg gcctggtgga ctttctcgtg atagagcagg ttttgaggtt   1680
cgtgacgttc attattctca ctacggtcgt atgtgcccca ttgaaacacc ggaaggtcca   1740
aacattggtc tcattctttc catgtctagt tttgcacgtg tgaacgatta tggattcatt   1800
gaaactccat accgccttgt aaagaatgga aaagtccaaa acaagtggaa atacctcact   1860
gcggacaaag aagaatacca ttatatggcg cagtcaaatt cgactgtgga tgagaaggga   1920
gaattcactt ccaaactcat ttccactcgt catagagggg atttcccttt ccgtagccca   1980
gctgaaatcc aatacatgga tcttgctccc ttgcaagtgg tctcagtttc cacagctctc   2040
attccgttct tagaacatga tgacgcgaac cgtgccctca tgggttccaa catgcaacgc   2100
caagcggtac cactcttaac agaagaggct ccttttgtcg gaactggtat ggaagctcgt   2160
gcggcttatg acgcaggggt ttgtatcgtt gcgaaaaaag atggtgtggt ttccaaagtg   2220
gatgcaacag gtgtttggat caagaagac caatccaaag agattgtcca ttacccactc   2280
attaaattca aaaaaccaa ccaaggtact tgttttaacc aaaaaccaaa cgtatccatg   2340
ttacacacca caactggtgg caaggtaagt aaggtttcga agaacgtgt cgaagtgaca   2400
actcctaacg gagaaaaga aactcatgaa cttcttcttt ctgatgaagt tcagttccat   2460
gctgttgtca agaaggaca agaggtagga attggagctc cagttgccgg acaaatcatc   2520
aaagggaaa aatacggtga cttcggtcag atccttcaaa aggaactgt cctagccaac   2580
gggccatcca ctgacgctgg gtatttggca cttggacgaa atgttctcgt tgcctttatg   2640
ccttgggaag gatacaactt tgaggatgcg attttaattt ctgaacgaat catcaaagac   2700
```

```
gatgttttct cttccatcca cattgaagaa ttcgaaatcc aagctcggga aacgaaactc    2760
ggacaagaac aaatcactcg tgacattcca aacctttcgg acaaagcgtt ccgtgatttg    2820
gatgagtctg gtgtgatccg tgtgggtgca gaggtaaaac ctggagacat cctagttggg    2880
atggtgactc caaaagggga aacagacctc acacctgaat acaaactatt acactccatt    2940
tttggagaga aggcaaaaga agttagggat tcctcactcc gtatgccaaa cggtttcgaa    3000
ggaactgtca tcgatatcaa acgttattcc cgtgaaacag gcgatgaact cgctgctggc    3060
gtggaagaaa tggtaaaagt ttacgtggct cgcaaacgga aactcctcgt gggtgataag    3120
atggccggaa gacacgggaa caaggggtc gtagcacgtg tgatggcaca agaagatatg    3180
ccatacatgg aagacggatc tccagttgac atcgtactca acccactcgg tgttccttcg    3240
cgtatgaacc tcggtcagat ctttgaaact caacttggat ttgctgcaaa aaactaggg    3300 atcaattttg aaacccctgt gtttgacgga gcttccgaag gtgatgtaaa cgatttctgc    3360 aaaaagcag gattaccgga aaacagcaaa tttcagttat atgatggaag gactggtgaa    3420
aaattcatca accaagtatt ctgtggatac atttacatgt tgaaactggc tcacttggtg    3480
gatgacaaaa ttcacgcaag atccactgga ccttactcac tcgtaacaca caaccactg    3540 ggtggtaagg cgcagttcgg gggacaaagg ttaggggaga tggaagtttg ggcactcgaa    3600
gcatacggtg cctcacacac cttacaagaa ttactgacca tcaagtcaga tgacatgctc    3660
ggacgtgcca gaatttacga agcaattgtg aaagggatcc actcgatcaa accgggtatc    3720
cctgaatcct tcaacgttct tgtacaagaa ctccgaggtc tcgcacttga tatcatcatc    3780
aaagactccg aaggattgga agtggatatc tctgattacg aagatgagtt ctcgaaaaac    3840
aaaaagaaaa ttaaattcga gaccattgaa aacgtt                              3876

<210> SEQ ID NO 6
<211> LENGTH: 914
<212> TYPE: DNA
<213> ORGANISM: Leptospira icterohaemorragiae

<400> SEQUENCE: 6
ttcactattc tcactacggt agaatgtgtc cgattgaaac tccggaaggt ccgaacatcg     60
gtctgattct ttccatgtct tcttacgctc gtgtgaatga ctacggattc ttggaaactc    120
cttacagaac cgtgaagaac ggtaaagtta ccggtcagat cgagcacctt accgcagaca    180
aagaagaata tcattacatc gctcaagctt ccggcgtgat cgatgaaaaa ggcgagctca    240
aaaacaaatt gatttccacg cgtcacagag ggatttccc tttccgtaac ccgagcgaga     300
ttcagtatat ggacttggck cctctacaag tcgtttcggt ttccacggcg ctgattccgt    360
tccttgaaca cgacgacgcg aaccgcgcct catgggttcc aacatgcaac gtcaggcggt    420
tcctcttctc cgtgaagaag ctcttttgta ggaactggta tggaaaccag agccgcttac    480
gattccagaa tttgtatcgt aaacaaacac gacggtgtcg taacttccgt cgatgcggaa    540
aacatcgttg tagaaagaaa gggcggaaaa gaatccgata cgtatcaact tacgaaattc    600
aaaaagacaa accaaggaac tgctttaatc agaagccgat tgtaggagtg gttcactccg    660
agatcaatgg aaaggtttcc aaggtttcca aagaaaaaat cgaagtcact ggtgaaaacg    720
gtgaactgaa agaatatgtt cttcaaatcg gaagcaaaca atattctccg atcgtctctg    780
caggcgaaga agtaaaaaga ggatcgactc tcgcaggaca agttgttgta ggtgagaagt    840
tggatgagat gggaaatatc ctcgtaaaag gaaccgttct tgctgatggt cctgcggtcg    900
acaacggagt tctc                                                      914
```

<210> SEQ ID NO 7
<211> LENGTH: 949
<212> TYPE: DNA
<213> ORGANISM: Leptospira biflexa

<400> SEQUENCE: 7

| | | | | | |
|---|---|---|---|---|---|
| gtgacgttca | ctattctcac | tacggtagaa | tgtgtccgat | tgaaactccg | gaaggtccga | 60 |
| acatcggtct | gattctttcc | atgtcttctt | acgctcgtgt | gaatgactac | ggattcttgg | 120 |
| aaactcctta | cagaaccgtg | aagaacggta | aagttaccgg | tcagatcgag | caccttaccg | 180 |
| cagacaaaga | agaatatcat | tacatcgctc | aagcttccgg | cgtgatcgat | gaaaaaggcg | 240 |
| agctcaaaaa | caaattgatt | ccacgcgtc | acagagggga | tttcccttc | cgtaacccga | 300 |
| gcgagattca | gtatatggac | ttggctcctc | tacaagtcgt | ttcggtttcc | acggcgctga | 360 |
| ttccgttcct | tgaacacgac | gacgcgaacc | gcgccctcat | gggttccaac | atgcaacgtc | 420 |
| aggcggttcc | tcttcttcgt | gaagaagctc | cttttgtcgg | aaccggtatg | gaaaccagag | 480 |
| ccgcttacga | ttccagaatt | tgtatcgtaa | acaaacacga | cggtgtcgta | acttccgtcg | 540 |
| atgcggaaaa | catcgttgta | gaaagaaagg | gcggaaaaga | atccgatacg | tatcaactta | 600 |
| cgaaattcaa | aaagacaaac | caaggaacct | gctttaatca | gaagccgatt | gtaggagtgg | 660 |
| ttcactccga | gattaacgga | aaggtttcca | aggtctccaa | agaaaaaatc | gaagtcactg | 720 |
| gtgaaaacgg | tgaactaaaa | gaatatgttc | ttcaaatcgg | aagcaaacaa | tattctccga | 780 |
| tcgtctccgc | aggcgaagaa | gtaaaacgag | gatcgactct | cgcaggacaa | gttgttgtag | 840 |
| gtgagaagtt | ggatgagatg | ggaaatatcc | tcgtaaaagg | aaccgttctt | gctgatggtc | 900 |
| ctgcggtcga | caacggagtt | ctcgctctgg | gaagaaacgt | tctcgcggc | | 949 |

<210> SEQ ID NO 8
<211> LENGTH: 800
<212> TYPE: DNA
<213> ORGANISM: Borrelia recurrentis

<400> SEQUENCE: 8

```
aagggatcga gcagctttga agtaagatat gtacattata cccattatgg taggatgtgt     60
cctattgaaa ctcctgaagg cccaaatatt ggacttattg tttctttggc tacttattca    120
aaagttaatg attatggttt cttagaaact ccttatagga aggtgattga tggtaaggtg    180
accgatgata ttgaatattt gtctgctatt gatgaggaaa aaaaatgtat tgcgcaagca    240
aatgcttctg ttagttctga tggtaattat actgatgatt tggtgtctgt taggatttct    300
ggggattata ctacaatgat gcctaaaaat atcgattaca tggatgtttc gcctagacaa    360
ttaatatctg tctcttcggc gttaatactt ttcttgaaca taatgatgca aatcgtgctc    420
ttatgggttc gaatatgcaa cgtcaggcag ttcttattat ttccacagcc acctattgtt    480
ggtacaggta tggagaggat agttgcaaaa gactctggtg ttgttattaa agcaaaaaga    540
cctggtagag ttgtcttagc cacaaacaaa aagatagtta ttaaacctga taatgcaact    600
tctgaacgag atttagatga atatgaactt tataaatatg agaggacaaa ccaggatact    660
tctttcaatc attcagtttt ggtgaagaat ggccaaattg ttaataagga tgagataata    720
gcagatggtc ctgctactag atatggagaa ttggcgcttg gtaataattt attagttgtt    780
ttattccgtg gaatggattt                                                800
```

SINGLE STRANDED OLIGONUCLEOTIDES, PROBES, PRIMERS AND METHOD FOR DETECTING SPIROCHETES

This invention concerns the techniques for the detection and/or amplification and sequencing, using probes or oligonucleotide primers, and the application of these probes or primers to detect or identify bacteria in the order of Spirochaetales (spirochetes).

In certain diagnostic tests, in particular during the search for a human or animal infection in the nervous system or a search after an arthropod bite, for example, it is often necessary to obtain a fast response concerning the presence of bacteria, and more specifically spirochetes, in a sample. However, the techniques currently developed, such as direct examination after Gram coloration or culture often fail due to the lack of Gram colour and the lack of growth in the culture medium.

In the case of spirochetes, forming a family of bacteria including the species *Leptospira, Borrelia, Treponema* and *Serpulina*, responsible for infectious diseases, such as meningoencephalitis, a culture is not possible. Therefore, the identification of spirochetes has still not been solved.

Given the increase in infectious diseases over the last twenty years and the dramatic consequences of these infectious diseases, it is necessary to develop a fast and specific method to detect infectious pathogenics such as spirochetes.

A possible solution, able to palliate the impossibility of the culture of bacteria, lies in the use of technologies related to nucleic acids and genetic material, in particular PCR (Polymerase Chain Reaction) methods, in order to determine whether a gene, a part of a gene or a nucleotide sequence is present in a living organism, a cell extract from this organism or a sample. Given that any gene or part of a gene is characterised by a specific sequence of nucleotide bases, it is therefore possible to directly search for the presence of all or part of the said specific sequence within a sample containing a mixture of polynucleotides.

Different types of methods for the detection of nucleic acids are described in the literature. These methods are based on the properties of purine-pyrimidine pairing of complementary stands of nucleic acids in the DNA—DNA and RNA—RNA duplex. This pairing process is carried out by the establishment of hydrogen bonds between adenine-thymine (A-T) and guanine-cytosine (G-C) bases of the double strand DNA. Pairs of adenine-uracile (A-U) bases may also form by hydrogen bond in the DNA-RNA or RNA—RNA duplex. The pairing of strands of nucleic acid to determine whether a given molecule of nucleic acid is present or absent is commonly called "hybridation of nucleic acids" or simply "hybridation".

An example of the PCR method includes the determination of a sequence on the base of RNAr 16S. However, this method has limits due to potential problems of contamination that hinder the diagnosis.

To make up for this disadvantage, new genetic markers have been found for the specific detection of bacteria belonging to the order of spirochetes in any sample, without a preliminary stage of bacteria culture. These new markers or oligonucleotides are the object of the invention.

The determination of these new markers relies on the use of specifically defined sequences in the gene rpoB of spirochetes coding for the β sub-unit in bacterial RNA polymerase. In fact, zones that vary according to the bacteria family but that appear preserved among the order of spirochetes are found on DNA coding for the β sub-unit of bacterial RNA polymerase. Therefore, this bacteria family can be distinguished from other bacteria families. The observation that, in the said preserved zones, there are minor variations of sequences between certain species of spirochetes was used to develop, these markers specific to the order of spirochetes.

According to Lazcano et al. [J. Mol. Evol. (1988) 27:365–376], the RNA polymerase are divided into two groups according to their origin, one formed by viral RNA- or DNA-dependent RNA polymerase and the other formed by DNA-dependent RNA polymerase of eucaryote or procaryote origin (archaebacteria and eubacteria). The DNA-dependant eubacteria RNA polymerase are characterised by a simple and preserved multimeric constitution called "core enzyme", represented by $\alpha\beta\beta'$ or "holoenzyme" represented by $\alpha\beta\beta'\sigma$ [Yura and Ishihama, Ann. Rev. Genet. (1979) 13:59–97].

A great many studies have revealed the functional role, within the multimeric enzyme complex, of the β sub-unit of eubacteria RNA polylmerase. Archaebacteria and eucaryote RNA polymerase present a more complex structure that may include ten or even thirty sub-units [Pühler et al., Proc. Natl. Acad. Sci. USA (1989) 86:4569–4573].

The genes that code for the different $\alpha\beta\beta'\sigma$ sub-units of DNA-dependent RNA polymerase in eubacteria, respectively genes rpoA, rpoB, rpoC and rpoD, are classified in different groups including genes coding for the proteins that constitute ribosome sub-units or for the enzymes involved in the duplication and repair of the genome [Yura and Ishihama, Ann. Rev. Genet. (1979) 13:59–97]. Certain authors have demonstrated that the nucleic sequences of genes rpoB and rpoC may be used to build phylogenetic trees [Rowland et al., Biochem. Soc. Trans. (1992) 21:40s] to separate the different branches and sub-branches among the kingdom of the living.

Before describing the invention in more detail, the different terms used in the description and claims are defined below:

"nucleic acid extracted from bacteria" refers to either the total nucleic acid or the genomic DNA or the messenger RNA or the DNA obtained from the reverse transcription of the messenger RNA;

"nucleotide fragment" or "oligonucleotide" are two synonymous terms indicating a sequence of DNA or RNA nucleotide motifs characterised by an informational sequence of natural (or modified) nucleic acids that are likely to hybrid, such as natural nucleic acids, with a complementary or a roughly complementary nucleotide fragment, in predetermined conditions of strict stringence. The sequence may contain nucleotide motifs with a different structure from that of natural nucleic acids. A nucleotide fragment (or oligonucleotide) may, for example, contain up to 100 nucleotide motifs. It generally contains at least 10, and in particular at least 12 nucleotide motifs and may be obtained from a natural nucleic acid molecule and/or by genetic recombination and/or by chemical synthesis;

"a nucleotide motif" is derived from a monomer that may be a natural nucleotide of nucleic acid where the constitutive elements are a sugar, a phosphate group and a nitrogen base chosen from among adenine, guanine, uracile, cytosine and thymine; or the monomer is a nucleotide modified in at least one of the former three constitutive elements. By way of example, the modification may occur in the bases, with modified bases such as inosine that can hybrid with any base A, T, U, C or G, methyl-5-deoxycytidine, deoxyuridine, dimethylamino-5-deoxyuridine or any other modified base able to hybrid, or in the sugar, for example, the replacement of at least one deoxyribose by a polyamide [P E Nielsen et al., Science, (1991) 254:1497–1500] or in the phosphate group, for example by replacement of chosen esters, in particular among diphosphates, alkyl and arylphosphonates and phosporothioates;

"informational sequence." refers to any ordered sequence of nucleotide motifs, where the chemical nature and the order in a reference direction form information similar to that provided by a sequence of natural nucleic acids;

"hybridation" refers to the process where, in appropriate conditions, two nucleotide fragments with sufficiently complementary sequences are able to associate by stable and specific hydrogen bonds, to form a double strand. The conditions for hybridation are determined by the "stringence", that is, the strictness of the operating conditions. The greater the stringence, the more specific the hybridation. The stringence is mainly a function of the composition in bases of a probe/target duplex, as well as by the degree of mis-matching between two nucleic acids. The stringence may also be a function of the parameters of the hybridation reaction, such as the concentration and type of ionic species found in the hybridation solution, the type and concentration of denaturing agents and/or the hybridation temperature. The stringence of the conditions in which the hybridation reaction has to be carried out mainly depends on the probes used. All of this data is well known and the appropriate conditions may eventually be determined in each case by routine experiments. In general, depending on the length of the probes used, the temperature for the hybridation reaction is approximately between 20 and 65° C., in particular between 35 and 65° C. in a saline solution at a concentration of about 0.8 to 1 µM.

a "probe" is a nucleotide fragment including, for example, between 10 and 100 nucleotide motifs, in particular between 12 and 35 nucleotide motifs, with a hybridation specificity in determined conditions to form a hybridation complex with a nucleic acid with, in the present case, a nucleotide sequence included in a messenger RNA or in a DNA obtained by reverse transcription of the said messenger RNA, a transcription product. A probe may be used for diagnostic purposes (in particular capture or detection probes) or for therapeutic purposes;

a "capture probe" is immobilised or can be immobilised on a solid support by any appropriate means, for example, by covalence, by adsorption, or by direct synthesis on a solid. Examples of supports include microtitration plates and DNA chips;

a "detection probe" may be marked by means of a marking agent chosen for example from among the radio-active isotopes, the enzymes, in particular enzymes able to act on a chromogenic, fluorigenic or luminescent substrate (in particular a peroxydase or an alkaline phosphatase), chromophoric chemical compounds, chromogenic, fluorigenic or luminescent compounds, analogues of nucleotide bases and ligands such as biotine;

a "species probe" is a probe that is able to identify the species of bacteria;

a "genus probe" is a probe that is able to identify the genus of a bacteria;

a "primer" is a probe including, for example, between 10 and 100 nucleotide motifs and with a hybridation specificity in determined conditions for the initiation of an enzyme polymerisation, for example, in an amplification technique such as PCR, in a sequencing procedure, in a transcription method, etc.

The first purpose of the present invention is a single stranded oligonucleotide chosen from among the oligonucleotides with a sequence of at least 12 consecutive nucleotide motifs included in one of the sequences SEQ ID NO 1 to SEQ ID NO 4 described in the list of sequences at the end of the description and among the complementary oligonucleotides of these oligonucleotides.

In each of the sequences SEQ ID NO 1 to 4, the nucleotide "N" mentioned in the list of sequences at the end of the description represents an identical or different nucleotide in each of the 3 positions where it appears and may represent inosine or an equimolar mixture of 4 different nucleotides chosen from among A, T, C and G or, should the occasion arise, A, U, C and G.

When "N" represents a said equimolar mixture of nucleotides at a given position, this means that the nucleotide at the said position indifferently represents A, T, C or G (or respectively, should the occasion arise, A, U, C or G) and that the oligonucleotide according to the invention more exactly consists of an equimolar mixture of 4 groups of oligonucleotides in each the said groups "N" has a different meaning at the said given position and respectively represents in each of the 4 groups A, T, C and G.

In each of the sequences SEQ ID NO 1 to 4, when in the 3 positions where a nucleotide "N" appears, N represents a said equimolar mixture of 4 nucleotides A, T, C and G (or N should the occasion arise A, U, C and G). The oligonucleotide forming the said sequence therefore represents a mixture of $4^3$ (64) oligonucleotides.

As indicated in the definitions, the oligonucleotide according to the invention may be in the form of an oligodeoxyribonucleotide (DNA) or an oligoribonucleotide (RNA) where, in this case, 'T' is replaced by "U".

In particular, an oligonucleotide according to the present invention has at least 12 motifs as described above and at not more then 50 motifs. Specifically, according to the present invention, an oligonucleotide has from 12 to 35 motifs.

A preferred oligonucleotide has a sequence chosen from among the sequences SEQ ID NO 1 to 4, or the complementary sequences.

Sequence SEQ ID NO 1, the sequence from the primer called primer NO 1, has 20 nucleic acids. Sequence SEQ ID NO 2, the sequence from the primer called primer NO 2, has 21 nucleic acids. Sequence SEQ ID NO 3, the sequence from the primer called primer NO 3, has 20 nucleic acids. Sequence SEQ ID NO 4, the sequence from the primer called primer NO 4, has 17 nucleic acids.

In the nomenclature referring to gene rpoB in *E. COLI*, the first nucleotides in sequences SEQ ID NO 1 to 4 correspond to the following positions:

SEQ ID NO 1:1 730,
SEQ ID NO 2:2 900,
SEQ ID NO 3:3 700,
SEQ ID NO 4:3 850.

The inventors discovered and revealed that the said sequences SEQ ID NO 1 to 4, as defined above, are not only consensual between the spirochetes, but that they are also specific to the family of spirochetes and enclose a fragment of gene rpoB including a very variable zone where the sequence is specific to the species and the genus serovar in a species of spirochete.

In fact, variable nucleotides in the complementary target sequences are found in the positions corresponding to those of nucleotides "N" in the sequences SEQ ID NO 1 to 4 as a function of the species of bacteria considered. However, the other nucleotides are preserved in all of the species of bacteria in the spirochete family. Since "N" represents inosine that may hybrid with any base, or an equimolar mixture of 4 bases A, T, C and G, an oligonucleotide or a mixture of oligonucleotides according to the invention always includes an oligonucleotide that can hybrid with a complementary target sequence of a spirochete bacteria.

In addition, since the sequences SEQ ID NO 1 to 4 enclose variable zones where the sequences are specific for each species of bacteria in the spirochete family, sequences SEQ ID NO 1 to 4 not only allow for the preparation of specific probes for the family of spirochetes, but also the detection and identification of the species of the said bacteria by PCR amplification by using the said sequences as primers.

In a mode of preparation of oligonucleotides according to the invention, "N" represents an inosine in all the positions.

In another mode of preparation, the oligonucleotide according to the invention represents a mixture of oligonucleotides (in particular $4^P$ oligonucleotides) comprising sequences included in one of the sequences SEQ ID NO 1 to 4, in which all of the nucleotides A, T, C and G are represented in each of the said positions where "N" appears (in particular p positions, p representing a whole number).

Sequences SEQ ID NO 1 to 4 may be prepared by chemical synthesis using familiar techniques described, for example, in the article by Itakura K. et al. [(1984) Annu. Rev. Biochem. 53:323].

A first application of an oligonucleotide from the invention is its use as a probe for the detection, in a biological sample, of bacteria belonging to the order of spirochetes that include a nucleotide sequence with at least 12 consecutive nucleotide motifs included in one of the sequences SEQ ID NO 1 to 4, and their complementary sequences. In the rest of the description, such a probe will be called a "genus probe".

According to the invention, the probes may be used for diagnostic purposes, in the search to determine whether a target nucleic acid is present in a sample, according to all known hybridation techniques and in particular the so-called "DOT-BLOT" techniques involving the deposit on a filter [Maniatis et al. (1982) Molecular Cloning, Cold Spring Harbor], the so-called "SOUTHERN BLOT" techniques involving DNA transfer [Southern, E. M., J. Mol. Biol. (1975) 98:503], the so-called "NORTHERN BLOT" techniques involving RNA transfer, or the so-called "sandwich" techniques [Dunn A. R., Hassel J. A. (1977) Cell 12:23]. In particular, the "sandwich" technique is used with a capture probe and/or a detection probe, the said probes are able to hybrid with two different regions of target nucleic acid, and at least one of the said probes (generally the detection probe) is able to hybrid with a region in the target that is specific to the species or group of species searched for, considering that the capture probe and the detection probe have to have at least partially different nucleotide sequences.

The nucleic acid to detect (target) may be DNA or RNA (one of them possibly obtained after PCR amplification). In the case of the detection of a double strand nucleic acid target, it is advisable to proceed with the denaturation of the latter before the use of the detection procedure. The target nucleic acid may be obtained by extraction according to the known methods for nucleic acids from a test sample. The denaturation of a double strand nucleic acid may be carried out by the familiar methods of chemical, physical or enzyme denaturation, and in particular by heating at an appropriate temperature above 80° C.

To use the aforementioned hybridation techniques, and in particular the "sandwich" techniques, a probe from the invention, called a capture probe, is immobilised on a solid support, and another probe from the invention, called a detection probe, is marked with an agent.

The examples of support and marker agent are defined above.

Another purpose of the invention is a method to determine whether at least one spirochete is present in a sample containing or likely to contain nucleic acids from at least one such bacteria, including the steps consisting in putting in contact the said sample with at least one genus probe from the invention, then to determine in a known manner whether a hybridation complex has formed between the said probe and the nucleic acid from the sample.

Examples of detection of the formation or lack of formation of a hybridation complex between the said probe and the nucleic acid include the techniques described above, that is, the "DOT-BLOT", "SOUTHERN-BLOT" and "sandwich" techniques.

In one specific use of this procedure to determine whether or not a species or a group of species of spirochete are present, a genus probe from the invention and a species probe from the invention are used. Of course, the said genus and species probes are able to hybrid with the non-overlapping regions of a nucleic acid corresponding to the gene rpoB of spirochetes.

In an advantageous way, the genus probe is immobilised on a solid support and the species probe is marked with a marking agent.

The present invention also involves the application of the procedure from the invention to determine the presence of a determined spirochete species.

In fact, the results of the research, revealing alignments of sequences preserved in spirochete species, according to the CLUSTAL method of alignment [Higgins D. G. & Sharp P. M. (1989) Gene 73:237–244], the said sequences have 1170 bases located between positions 1730 and 2900 of gene rpoB by referring to the numbering of *Escherichia coli* gene rpoB ATCC 25290, allow for the detection of at least one bacteria in the order of spirochetes. The use of probes containing zones muted for a specific species (with respect to the reference species, in this case *E. coli*) makes it possible to directly detect such a species. The sandwich hybridation techniques, using a combination of two probes (capture probe and detection probe), use, for example, a combination of a probe specific for the family of spirochetes and a probe specific for the species considered. It is also possible to use a combination of two probes specific for the said species. When they exist, these two probes are complementary for non-overlapping regions of the gene rpoB.

Another application of an oligonucleotide in the invention is its use as a nucleotide primer including a single stranded oligonucleotide chosen from among the oligonucleotides with a sequence of at least 12 nucleotide motifs included in one of the sequences SEQ ID NO 1 to 4, that can be used in the synthesis of a nucleic acid in the presence of a polymerase by a known procedure, that is in the methods of amplification using such a synthesis in the presence of a polymerase (PCR, RT-PCR, etc.). In particular, a primer from the invention may be used for the specific reverse transcription of a sequence of messenger RNA of at least one species or at least a group of species of spirochetes to obtain a corresponding complementary sequence of DNA. Such a reverse transcription may be the first stage in the RT-PCR technique, the following stage being the amplification of the complementary DNA obtained by PCR. It is also possible to use primers from the invention for the specific amplification by chain polymerisation reaction of the DNA sequence of the gene rpoB of at least one species or at least a group of species of spirochetes.

In a specific case, since the said primer comprises an oligonucleotide from the invention it also includes the direction or anti-direction sequence of a promotor recognised by a RNA polymerase (for example, promotors T7, T3, SP6 [Studier F W, B A Moffatt (1986) J. Mol. Biol. 189:113]. Such primers can be used in the methods to amplify nucleic acid involving a transcription stage, such as, for example, the NASBA or 3SR techniques [Van Gemen B. et al. Abstract M A 1091, 7th International Conference on AIDS (1991), Florence, Italy].

Another purpose of the invention is a nucleotide primer comprising a single stranded oligonucleotide chosen from among the oligonucleotides with a sequence of at least 12 consecutive nucleotide motifs included in one of the sequences SEQ ID NO 1 to SEQ ID NO 4 that can be used for the total or partial sequencing of the gene rpoB in any species of spirochete. In particular, the nucleotide primer can be used for the sequencing of an amplified nucleic acid.

In fact, the oligonucleotide primers concerned by the invention allow for the amplification and then the sequencing of the gene rpoB in all spirochetes, and the identification of any spirochete by bio-data processing analysis of this sequence and the recognition of new and unknown species of spirochetes. The sequencing involves the acquisition of the total or partial sequence of the gene rpoB by a familiar method, absorptive polymerisation using di-deoxynucleotides [Sanger F., Coulson A. R. (1975) J. Mol. Biol. 94:441] or multiple hybridiations using DNA chips.

Primers NO 1 to NO 3 can be used as 5' primers and primers NO 2 to NO 4 as 3' primers to amplify a fragment of gene rpoB enclosed in 5' and 3' by the said primers.

In one mode, a set of two primers is used consisting of two different oligonucleotides chosen from among the oligonucleotides with a sequence of at least 12 nucleotide motifs included in sequences SEQ ID NO 1 to 3 for 5' primer and SEQ ID NO 2 to 4 for 3' primer.

The present invention also includes a method, characterised in that the fragment of gene rpoB of the said bacteria is first amplified with primers according to the invention, then the said fragment is put into contact with a probe from the said bacteria according to the invention. Whether or not a hybridation complex is formed between the said probe and the said fragment is determined.

The present invention also involves a method to determine whether at least one bacteria in the order of spirochaetales is present in a sample containing or likely to contain nucleic acids from at least one such bacteria, characterised in that the said sample is put into contact with primers according to the invention. Amplification is then carried out and whether or not an amplification product appears is determined.

In one mode, a method to determine whether at least one bacteria from the order of spirochaetales is present in a biological sample containing or likely to contain nucleic acids from the said bacteria, is characterised in that the method amplifies and carries out the sequencing of a fragment of gene rpoB of the said bacteria in the said sample by means of primers according to the invention and the sequence of the fragment of gene rpoB of the gene obtained is compared with the known sequence of a fragment of gene rpoB of the said bacteria in a sample if the sequence of the fragment obtained is identical to the known sequence of the fragment of gene rpoB of the said bacteria.

The present invention also involves a detection probe, in a biological sample, specific for a species of bacteria belonging to the order of spirochaetales, characterised in that it includes a fragment of gene rpoB that can be obtained by amplification by means of primers according to the invention, preferably with one of the sequences SEQ ID NO 1 to 3 as 5' primer and one of the sequences SEQ ID NO 2 to 4 as 3' primer. The said fragment of gene rpoB enclosed by the oligonucleotides according to the invention actually corresponds to a very variable zone according to the species of said bacteria belonging to the order of spirochaetales and that is specific for each said species.

Finally, the invention also includes a gene therapy probe to treat infections induced by at least one species or a group of species of spirochetes, the said probe including an oligonucleotide as defined above. This gene therapy probe, able to hybrid on the messenger RNA and/or on the genome DNA of the said bacteria, can block the translation and/or transcription and/or duplication phenomena.

The principle of the gene therapy methods is known and is mainly based on the use of a probe corresponding to an anti-direction strand. The formation of a hybrid between the probe and the direction strand is able to perturb at least one of the stages in the decoding of the genetic information. Gene therapy probes can thereby be used as anti-bacteria drugs, to fight infections caused by spirochetes.

The invention will now be described in detail using the following experimental report.

The following description will better be understood using FIGS. 1 and 2 in which.

The strains of spirochetes used in the following examples, that is *Borrelia burgdorferi, Borrelia recurrentis, Treponema pallidum, Leptospira biflexa serovar patoc* (hereafter called *Leptospira biflexa*), *Leptospira interrogans serovar icterohaemmorragiae* (hereafter called *Leptospira icterohaemmorragiae*) and *Leptospira interrogans serovar australis* (hereafter called *Leptospira australis*), have all been obtained from the ATCC collection, except for *Borrelia recurrentis* that is available at the Centre National de référence, Institut Pasteur Paris (France). The ATCC number of *Borrelia burdorferi* is 35210, that of *Treponema pallidum* is 27087, that of *Leptospira biflexa* is 23582, that of *Leptospira icterohaemmorragiae* is 43642 and that of *Leptospira australis* is 23605.

The *Borrelia* and *Leptospira* strains were grown at 30° C. on BSKII and EMJH media, respectively [Barbour A. G. (1984) Yale J. Biol. Med. 57:521]. Since *T. pallidum* can not be grown in vitro, this pathogenic bacteria was propagated by injection in the testicles of a rabbit.

The other strains of bacteria used, *Escherichia coli, Staphylococcus aureus, Streptococcus salivarius* and *Pseudomonas aeruginosa* were clinically isolated from patients hospitalised in Marseille.

EXAMPLE 1

Specific Detection of Spirochetes Using Probes from the Invention

This experiment was carried out with the following spirochete strains: *Borrelia burdorferi, Treponema pallidum, Leptospira biflexa, Leptospira icterohaemmorragiae, Leptospira australis* and *Borrelia recurrentis*, as well as with *Staphylococcus aureus*.

A mixed bacteria suspension was prepared by mixing a spirochete DNA with a extract of *Staphylococcus aureus*.

A PCR method was carried out using the QIAamp tissue kit (Qiagen) and the Gibco Polymerase Taq (Gibco BRL, USA). After a first stage of determination (94° C. for 2 minutes), a cycle of 3 stages consisting of 94° C. for 30 s, 52° C. for 30 s and 72° C. for 1 minute was repeated 35 times. The PCR programme was terminated. The resulting amplicons were purified and sequenced as indicated above.

Figure 1:
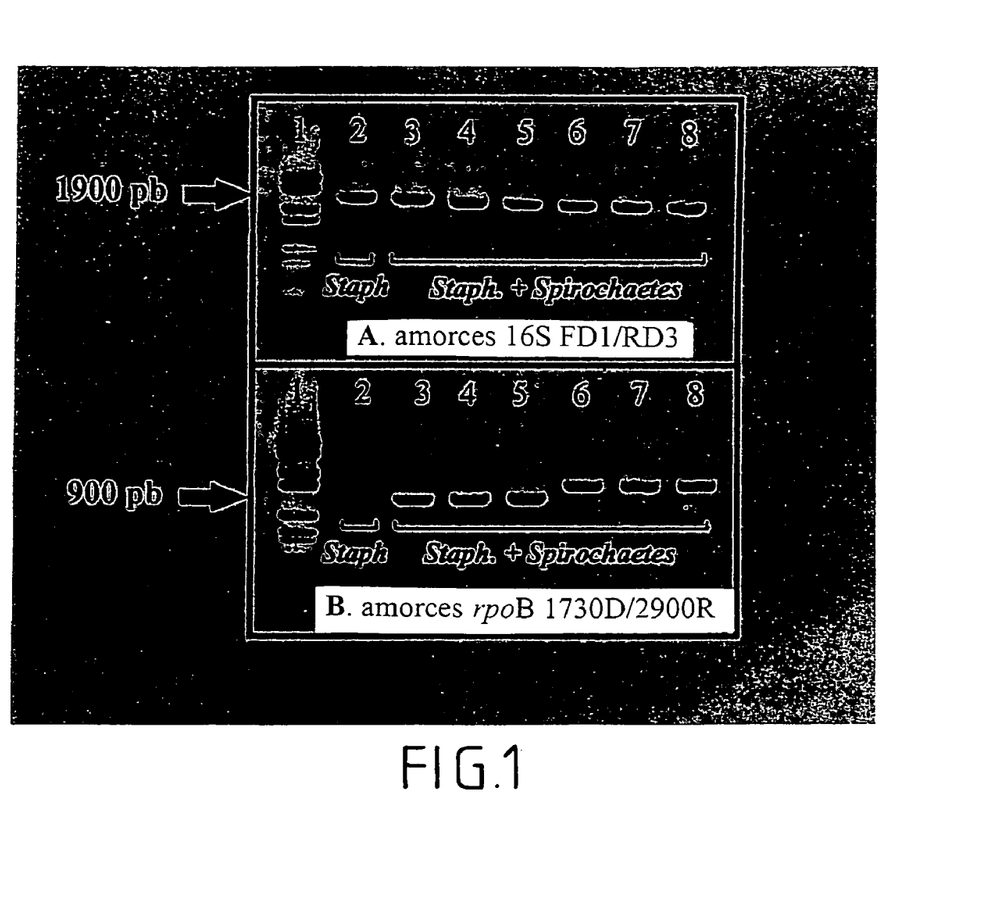
FIG. 1 is a photo of an electrophoresis gel revealing the detection of spirochetes in a mixed bacteria suspension using the probes in the invention.

The results are indicated in FIG. 1, in which:

band 1 corresponds to molecular mass markers (Boehringer), band 2 corresponds to *S. aureus* alone, band 3 corresponds to *B. burgdorferi*+*S. aureus*, band 4 corresponds to *B. recurrentis*+*S. aureus*, band 5 corresponds to *T. pallidum*+*S. aureus*, band 6 corresponds to *L. biflexa*+*S. aureus*, band 7 corresponds to *L. australis*+*S. aureus*, band 8 corresponds to *L. icterohaemmorragiae*+*S. aureus*.

The following primers were used:

panel A: RNAr primers 16S FDI and RD3 [Weisburg et al. J. Bacteriol. (1991) 173:697–703].

panel B: the primers 1730D and 2900R from the invention.

The primer 1730D in sequence SEQ ID NO 1 (5'CTTG-GNCCNGGNGGACTTTC3') in which "N" is inosine and the primer 2900R has the sequence SEQ ID NO 2 (5'AGAAATNAANATNGCATCCTC3') in which "N" is inosine.

The results show that the primers in the invention were not able to amplify the DNA of *S. aureus* alone, and therefore detect *S. aureus*, but were able to amplify that of the spiochetes, and thereby detect it, even in the presence of *S. aureus* (panel B), as opposed to primers 16S that were able to amplify the DNA only in *S. aureus* (panel A).

EXAMPLE 2

Specific Amplification of Fragments of Gene rpoB Using the Primers in the Invention This experiment was carried out with the following spirochete strains: *Borrelia burdorferi*, *Treponema pallidum*, *Leptospira biflexa*, *Leptospira icterohaemmorragiae*, *Leptospira australis* and *Borrelia recurrentis*, as well as with the other non-spirochete strains *Escherichia coli*, *Staphylococcus aureus*, *Streptococcus salivarius* and *Pseudomonas aeruginosa*.

The sequence of the gene rpoB in *Treponema pallidum* used is that described by Weinstock et al. [(1998) The genome of *Treponema pallidum*: new light on the agent of syphilis. FEM Microbiol. Rev. 22:323–332].

The sequence of gene rpoB in *Borrelia burgdorferi* used is that described by Alekshun et al. [(1997) Molecular cloning and characterisation of *Borrelia burgdorferi* rpoB. Gene 186:227–235].

The DNA sequence of the gene rpoB of *Leptospira biflexa*, *Leptospira icterohaemmorragiae*, *Leptospira australis* and *Borrelia recurrentis* were obtained by PCR in the following way:

The genome DNA of *Leptospira biflexa* was extracted according to the standard procedures with phenol/chloroform [Sambrook et al. (1989) Molecular Cloning: A Laboratory Manual. Cold Spring Harbour, N.Y.]. In this first stage of the experiment, amplifications by PCR were carried out with primers SEB1 (5'-AAC CAG TTC CGC GTT GGC CTG G-3') and SEB2 (5'-CCT GM CM CAC GCT CGG A-3') (SEB for *Staphylococcus aureus*, *Escherichia coli* and *Borrelia subtilis*) and the polymerase DBA Taq by Eurogentec (Seraing, Belgium) by using 5 µl of DNA for a final volume of 50 µl. After a first stage of denaturation (95° C. for 1.5 min), a cycle was repeated 35 times consisting of 3 stages of 95° C. for 20 s, 50° C. for 30 s and 72° C. for 1 min. The PCR programme was completed with a single stage of extension of 3 min at 72° C. (Peltier PTC 200 heat cycle model, MJ Research, Watertown, Mass., USA).

The amplicons obtained by electrophoresis were then separated on 1% agarose gel and they were visualised by coloration with ethidium bromide.

The sequencing of the gene was then carried out by pruification of the samples with the PCR QIAquick purification kit (Qiagen, Hilden, Germany) and they were allowed to react with the dRhodamine Terminator Cycle Sequencing Ready Reaction buffer (DNA sequencing kit, Perkin-Elmer). Finally, the electrophoresis of the reactive products was carried out with the automatic Applied Biosystems DNA sequencor model ABI 310 (Perkin-Elmer).

The sequence of the 5' end of gene rpoB was obtained by using a Universal Genome Walker™ kit (Clontech, Palo Alto, Calif., USA) in the following manner. Five groups of genome DNA fragments called Genome Walker "banks" were built by using DraI, EcoRV, PvuII, ScaII and StuI restriction enzymes. These banks were used for the prior sequencing of the genome DNA by using a specific primer for the gene whose sequence corresponds to the region as close as possible to the known 5' end of the gene and an adaptation primer supplied by the kit.

The amplified fragments were purified and a source of DNA was used for a second enclosed PCR. The amplicons obtained were then treated as described above for the automatic sequencing.

Gene rpoB from the *Leptospira biflexa* obtained has the sequence SEQ ID NO 5 and has 3876 nucleic acids. Gene rpoB from the *Leptospira icterohaemorragia* obtained has a sequence SEQ ID NO 6 and has 914 nucleic acids. Gene rpoB from the *Leptospira australis* obtained has the sequence SEQ ID NO 7 and has 949 nucleic acids. Finally, gene rpoB from the *Borrelia recurrentis* obtained has the sequence SEQ ID NO 8 and has 800 nucleic acids.

The DNA sequences of the gene rpoB from *Escherichia coli*, *Staphylococcus aureus*, *Streptococcus salivarius* and *Pseudomonas aeruginosa* are described in the literature (Gene Bank).

The fragments of gene rpoB to amplify consisted of 949 pb.

The amplifications of the fragments of gene rpoB by PCR were carried out as in example 3, except that each species was used separately.

Figure 2:
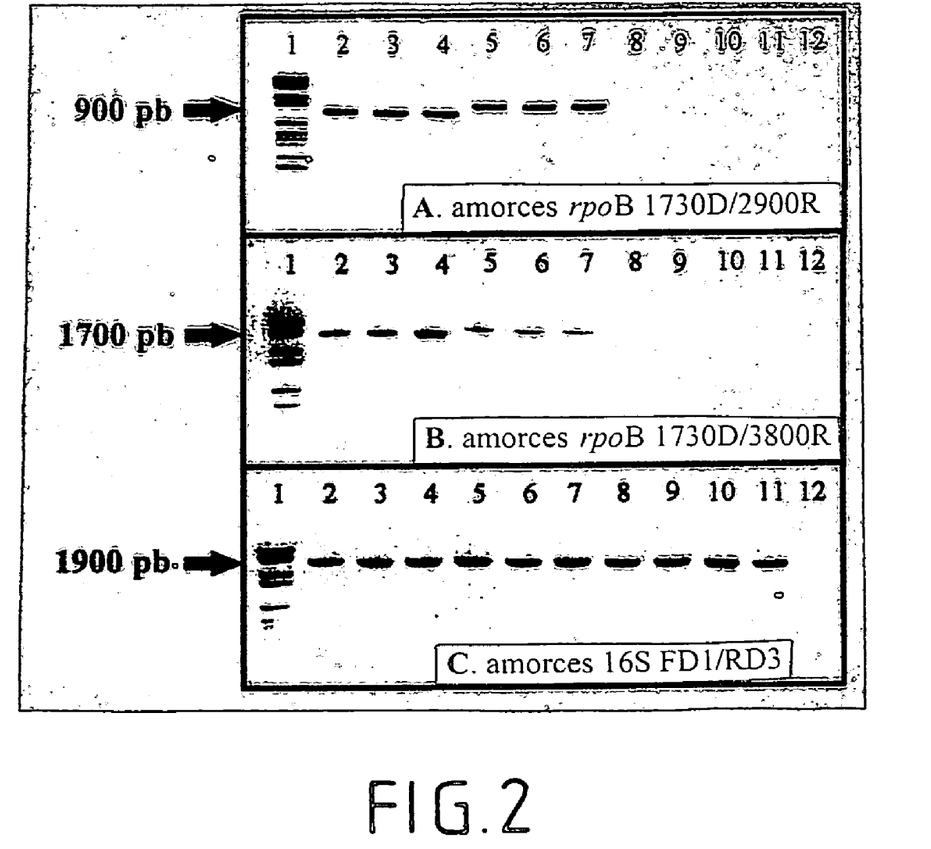
FIG. 2 is a photo of an electrophoresis gel revealing the specific amplification by PCR of fragments of gene rpoB of spirochetes by using the primers in the invention.

The results are indicated in FIG. 2 where:

band 1 corresponds to the molecular mass markers (Boehringer), band 2 corresponds to *B. burgdorferi*, band 3 corresponds to *B. recurrentis*, band 4 corresponds to *T. pallidum*, band 5 corresponds to *L. biflexa*, band 6 corresponds to *L. australis*, band 7 corresponds to *L. icterohaemmorragiae*, band 8 corresponds to *E. coli*, band 9 corresponds to *S. aureus*, band 10 corresponds to *Str. salivarius*, band 11 corresponds to *Ps. aeruginosa*, band 12 corresponds to a negative reference without DNA.

The following primers were used:

panel A: primer 1730D and primer 2900R from the invention, panel B: primer 1730D and primer 3800R from the invention and panel C: RNAr primers 16S RD1 and FD3.

Primer 3800R has the sequence SEQ ID NO 4 (5'GCT-TCNAGNGCCCANAC3') in which "N" is an inosine.

The results show that the primers in the invention only allowed for the amplification of the DNA fragments of spirochetes (panels A and B) while primers 16S amplified everything (panel C).

The primer SEQ IS NO 3 (5'GGGTGNATTTTNTCATC-NAC3') may also be used as a primer. Primers NO 1 and 3 according to the invention allowed for the amplification and then sequencing of the amplified product, the detection and identification of the bacteria *Borrelia duttonii* in which an African tick collected in ZAIRE of the species *ornithodoros moubata* and the total blood of a Zaire patient presenting a recurrent fever.

The invention claimed is:

1. An isolated oligonucleotide consisting of a sequence selected from the group consisting of SEQ ID NO: 1 to SEQ ID NO: 4 and sequences complementary thereto, wherein "n" represents inosine.

2. A mixture of 64 isolated oligonucleotides each consisting of a sequence selected from the group consisting of SEQ ID NO: 1 to SEQ ID NO: 4 and sequences complementary thereto, wherein "n" represents an equimolar mixture of the nucleotides a, t, c and g.

3. A method to determine whether bacteria belonging to the order of Spirochaetales is present in a sample containing or likely to contain nucleic acid from said bacteria, comprising:
 (a) contacting said sample with at least one probe comprising an oligonucleotide according to claim 1; and
 (b) determining whether a hybridation complex forms between said at least one probe and said nucleic acid in said sample.

4. A method according to claim 3, wherein said oligonucleotide is immobilised on a solid support.

5. A method according to claim 3, wherein said oligonucleotide is marked with a tracing agent.

6. A method to determine whether bacteria belonging to the order of Spirochaetales is present in a sample containing or likely to contain nucleic acid from said bacteria, comprising:
 (a) contacting said sample with at least one probe comprising a mixture of oligonucleotides according to claim 2; and
 (b) determining whether a hybridation complex forms between said at least one probe and said nucleic acid in said sample.

7. A method according to claim 6, wherein said oligonucleotides are immobilised on a solid support.

8. A method according to claim 6, wherein said oligonucleotides are marked with a tracing agent.

9. A method to determine whether bacteria belonging to the order of Spirochaetales is present in a sample containing or likely to contain nucleic acid from said bacteria, comprising:
 (a) contacting said sample with primers comprising oligonucleotides according to claim 1;
 (b) carrying out an amplification; and
 (c) determining the presence or absence of an amplification product.

10. A method to determine whether bacteria belonging to the order of Spirochaetales is present in a sample containing or likely to contain nucleic acid from said bacteria, comprising:
 (a) contacting said sample with primers comprising mixtures of oligonucleotides according to claim 2;
 (b) carrying out an amplification; and
 (c) determining the presence or absence of an amplification product.

11. A method according to claim 9 or 10, further comprising:
 (d) sequencing the amplified fragment when an amplification product is obtained; and
 (e) comparing the sequence of the amplified fragment with the known sequence of gene rpoB of the bacteria, wherein the species of the bacteria is determined if the sequence of the amplified fragment is identical to that of the known sequence.

* * * * *